(12) United States Patent
Roulier et al.

(10) Patent No.: US 6,264,965 B1
(45) Date of Patent: Jul. 24, 2001

(54) COMPOSITION IN THE FORM OF AN O/W EMULSION WITH A HIGH WAX CONTENT AND USES THEREOF IN COSMETICS AND DERMATOLOGY

(75) Inventors: Veronique Roulier, Paris; Pascal Simon, Seine, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/451,918

(22) Filed: Dec. 1, 1999

(30) Foreign Application Priority Data

Dec. 3, 1998 (FR) .................................................. 98 15293

(51) Int. Cl.⁷ ...................................................... A61K 7/00
(52) U.S. Cl. ............................ 424/401; 264/4.1; 264/4.3; 264/4.6; 424/78.02; 424/78.03
(58) Field of Search ................................ 424/401, 78.02, 424/78.03; 514/846, 847

(56) References Cited

U.S. PATENT DOCUMENTS

| | | | |
|---|---|---|---|
| 4,536,519 | 8/1985 | Suzuki et al. | 514/785 |
| 4,673,526 | * 6/1987 | Zabotto et al. | 252/174.16 |
| 4,959,233 | * 9/1990 | Schou et al. | 426/443 |
| 5,093,110 | * 3/1992 | Kamen et al. | 424/63 |

OTHER PUBLICATIONS

Maeno Kiyoshi, "Oil–In–Water Type Emulsifying Composition", Patent Abstracts of Japan, vol. 011, No. 133, Apr. 25, 1997.

\* cited by examiner

*Primary Examiner*—Gollamudi S. Kishore
*Assistant Examiner*—Liliana Di Nola-Baron
(74) *Attorney, Agent, or Firm*—Oblon, Spivak, McClelland, Maier, Neustadt, P.C.

(57) ABSTRACT

A creamy composition in the form of an oil-in-water emulsion comprising an oily phase dispersed in an aqueous phase, characterized in that it contains at least one anionic emulsifier which is liquid at room temperature, and at least 5% by weight of one or more waxes relative to the total weight of the composition, and in that the oily phase is in the form of a soft paste at room temperature. The anionic emulsifier is preferably a surfactant containing a phosphate group, such as octyldecyl phosphate. The present invention also relates to the uses of the said composition in cosmetics and dermatology, in particular for caring for, treating and/or making up the skin and/or mucous membranes, and more particularly for treating wrinkles and/or fine lines of the skin and/or for treating dry skin. The invention also relates to a process for preparing this composition, characterized in that at least one step of the process is carried out using a mixer-extruder.

22 Claims, No Drawings

COMPOSITION IN THE FORM OF AN O/W EMULSION WITH A HIGH WAX CONTENT AND USES THEREOF IN COSMETICS AND DERMATOLOGY

BACKGROUND OF THE INVENTION

1. Field of the Invention

The present invention relates to a composition in the form of an oil-in-water (O/W) emulsion comprising a high content of wax, and to its uses in cosmetics and dermatology, in particular for caring for, treating and/or making up the skin and/or mucous membranes, and more particularly for treating wrinkles and/or fine lines of the skin and/or for treating and/or protecting dry skin. The invention also relates to a process for preparing this composition, where at least one step of the process is carried out using a mixer-extruder.

2. Description of the Invention

It is well-known to use waxes in cosmetic creams in the form of emulsions intended for caring for human skin, in particular for the anti-wrinkle effects provided by these waxes. However, it is difficult to incorporate a high percentage of waxes into these compositions since waxes have a tendency to thicken the emulsions considerably. In addition, when a high percentage of waxes is incorporated into an emulsion, the emulsion is very difficult to apply to the skin since it does not slide. Moreover, a coarse effect appears on the skin. Such an emulsion is therefore unacceptable to users.

Furthermore, it is known to incorporate a high percentage of waxes into mascaras. However, compositions of this type cannot be used as care products on account of the drawbacks mentioned above.

Moreover, to prepare an emulsion containing waxes, it is necessary to melt the waxes in the fatty phase of the emulsion, in particular if it is desired, for example, to use waxes such as carnauba waxes which are particularly advantageous for their anti-wrinkle effect on the skin. It is thus necessary to heat the fatty phase up to 80–85° C., which is particularly harmful when it is desired to introduce heat-sensitive compounds.

Therefore, a need exists for a composition containing a high percentage of waxes which is free of the drawbacks of the compositions described above.

SUMMARY OF THE INVENTION

It is an object of the present invention to provide an oil-in-water emulsion that contains wax.

It is another object of the present invention to provide methods of treating skin, especially human skin, using the oil-in-water emulsion that contains wax.

The inventors having discovered, surprisingly, that a high percentage of waxes can be incorporated into O/W emulsions while at the same time retaining satisfactory fluidity and a pleasant sensation when it is applied to the skin, by preparing the emulsion without heating, using an anionic emulsifier which is liquid at room temperature and starting with a soft oily phase containing a high percentage of waxes.

Accordingly, the objects of the invention, and others, maybe accomplished with a creamy composition in the form of an oil-in-water emulsion and comprising:

an oily phase dispersed in an aqueous phase, at least one anionic emulsifier which is a liquid at room temperature, and at least 5% by weight, relative to the total weight of the composition, of at least one wax, where the oily phase is in the form of a soft paste at room temperature.

The objects of the present invention may also be accomplished with a method of treating wrinkles and/or fine lines of the skin, comprising applying an effective amount of the inventive composition to the skin.

The objects of the present invention may also be accomplished with a method of treating and/or protecting dry skin, comprising applying the effective amount of the inventive composition to the skin.

The objects of the present invention may also be accomplished with a method of preparing the inventive composition, comprising dispersing the oily phase in the aqueous phase.

The objects of the present invention may also be accomplished with a method of preparing the inventive composition, comprising:

(a) preparing the oily phase in the form of a soft paste by mixing the waxes and oils, (b) heating the oily phase to a temperature at which it melts, (c) introducing melted oily phase and the other constituents of the oily phase into a mixer-screw extruder subjected to a temperature gradient ranging from 80° C. to 20° C., (d) blending the mixture obtained while at the same time cooling it to room, temperature while it is conveyed to the outlet of the mixer-extruder to produce a soft paste, (e) incorporating the emulsifier and, optionally, if present, the co-emulsifier into the soft paste obtained from (d), and (f) incorporating the mixture from (e) into the aqueous phase.

A more complete appreciation of the invention and many of the attendant advantages thereof will be readily obtained as the same becomes better understood by reference to the following detailed description.

DETAILED DESCRIPTION OF THE INVENTION

The composition of the present invention is in the form of a cream, i.e. a soft product, as opposed to the solid structure of a stick. A cream has a viscosity at room temperature (about 20–25° C.) between 1 to 10 Pa.s, measured with a Rheomat 180. This range includes all specific values and subranges therebetween, such as 2, 3, 5 and 8 Pa.s.

Although containing a large amount of wax, the composition obtained feels fresh when applied.

The anionic emulsifier used in the composition of the invention is liquid at room temperature, i.e. at a temperature ranging from 15° C. to 25° C. It can be chosen in particular from the group of anionic surfactants containing a phosphate group, which are liquid at room temperature, such as mono-, di- and/or triesters of phosphoric acid and of a $C_{12}$ to $C_{22}$ fatty alcohol, i.e. of an alcohol having an alkyl chain containing from 12 to 22 carbon atoms (inclusive of all specific values and subranges therebetween, such as 14, 16, 18 and 20 carbon atoms), and mono-, di- and/or triesters of phosphoric acid and of an ethoxylated fatty alcohol, having a fatty chain containing from 12 to 22 carbon atoms (inclusive of all specific values and subranges therebetween, such as 14, 16 from 20 carbon atoms) and a number of ethoxylated units ranging from 1 to 100 and preferably from 4 to 25 (inclusive of all specific values and subranges therebetween, such as 2, 5, 10, 15, 35, 50, 75 and 90).

Anionic emulsifiers that are liquid at room temperature which are preferred are oleyl phosphate (mixture of mono- and diester of phosphoric acid and of oleyl alcohol), trioleyl phosphate, dilaureth-4 phosphate (mixture of diesters of phosphoric acid and of polyethylene glycol ether and of lauryl alcohol, containing 4 oxyethylenated groups), trioleth-8 phosphate (mixture of triesters of phosphoric acid and of ether of polyethylene glycol and of oleyl alcohol, containing 8 oxyethylenated groups), triceteareth-4 phosphate (mixture of triesters of phosphoric acid and of ether of polyethylene glycol and of cetyl and stearyl alcohols, containing 4 oxyethylenated groups), the monoester of phosphoric acid and of stearic and isostearic acid (CTFA name: octyldecyl phosphate) sold under the name Hostaphat CG 120 by Clariant, and mixtures thereof. According to one preferred embodiment of the invention, octyldecyl phosphate is used.

The amount of emulsifier in the composition according to the invention generally ranges from 0.1 to 10% by weight of active material and preferably from 1 to 5% by weight of active material relative to the total weight of the composition. These ranges includes all specific values and subranges therebetween, such as 0.2, 0.5, 2, 3, and 8% by weight.

A co-emulsifier can optionally be added to the anionic emulsifier which is liquid at room temperature, provided that the mixture of the emulsifier and the co-emulsifier is liquid at room temperature.

Co-emulsifiers which may be used include, for example, fatty alcohols comprising a branched or unsaturated chain containing from 8 to 22 carbon atoms (inclusive of all specific values and subranges therebetween, such as 10, 12, 14, 16, 18 and 20 carbon atoms), such as isostearyl alcohol, fatty acids comprising a branched or unsaturated chain containing from 8 to 22 carbon atoms (inclusive of all specific values and subranges therebetween such as 10, 12, 14, 16, 18 and 20 carbon atoms), such as ricinoleic acid, and mixtures thereof.

When the composition contains a coemulsifier, the amount of co-emulsifier generally ranges from 0.1 to 10% by weight of active material and preferably from 1 to 5% by weight of active material relative to the total weight of the composition. These ranges includes all specific values and subranges therebetween, such as 0.2, 0.5, 2, 3, and 8% by weight.

The composition of the invention contains, in the oily phase, at least 5% by weight of one or more waxes relative to the total weight of the composition. The oily phase, cooled before it is mixed with the aqueous phase, is advantageously in the form of a soft paste at room temperature (about 25° C.). The expression "soft paste" as used herein refers to a paste whose viscosity can be measured, as opposed to the solid structure of a tube or stick, whose viscosity cannot be measured. The dynamic viscosity of the soft paste at 25° C. is generally between 3 and 35 Pa.s, measured with a Contraves TV rotary viscometer fitted with an MS-r4 rotor at a frequency of 60 Hz. This range includes all specific values and subranges therebetween such as 5, 10, 15, 20, 25 and 30 Pa.s.

The fact that the oily phase is in the form of a soft paste at room temperature allows to prepare the emulsion (mixing of the oily and aqueous phases) without heating and to obtain a creamy composition which is easy to apply on the skin and pleasant to use, and this in spite of a large amount of waxes.

Examples of waxes which can be used in the composition of the invention include, for example, of mineral waxes such as microcrystalline waxes, paraffin, petrolatum, petroleum jelly, ozokerite, montan wax; animal waxes such as beeswax, lanolin and its derivatives; plant waxes such as candelilla wax, ouricury wax, carnauba wax, Japan wax, cocobutter, cork fibre wax or sugar cane wax; hydrogenated oils; fatty esters and glycerides which are solid at 25° C.; synthetic waxes such as polyethylene waxes and the waxes obtained by Fischer-Tropsch synthesis; silicone waxes, and mixtures thereof.

According to one preferred embodiment of the invention, at least one wax having a starting melting point of greater than or equal to 50° C., and better still at least one wax whose starting melting point is greater than 65° C., is used, such as carnauba wax, certain polyethylene waxes and certain microcrystalline waxes such as the one sold by Tisco as "Tisco Wax 88" or the one sold by RMC as "Feruwax 30540".

As used herein, the term "starting melting point" means the temperature at which a wax begins to melt. This temperature can be determined by DTA (differential thermal analysis), which allows the production of a thermogram (or melting curve) of the wax under consideration. The starting melting point corresponds to the temperature at which an appreciable change in the slope of the thermogram can be observed. The melting point itself represents the minimum point of the said thermogram.

The amount of wax(es) in the composition of the invention is at least 5% and preferably ranges from 5 to 30%, and better still from 5 to 15%, by weight relative to the total weight of the composition. These ranges includes all specific values and subranges therebetween, such as 10, 12, 18, 20 and 25% by weight.

The amount of oily phase in the composition of the invention generally ranges from 10 to 70% and preferably from 20 to 50% by weight relative to the total weight of the composition. These ranges includes all specific values and subranges therebetween, such as 15, 25, 30, 40 and 60% by weight. This oily phase is used in an amount such that, or else contains an amount of waxes such that, the amount of waxes in the final composition is greater than or equal to 5%.

The oily phase of the composition of the invention generally comprises, besides the wax(es), one or more fatty substances chosen from oils of animal origin, oils of plant origin, mineral oils, synthetic oils, fluoro oils, silicone oils and in particular volatile silicone oils, silicone gums, silicone resins, fatty alcohols, fatty acids and silicone elastomers such as the products sold as "KSG" by Shin-Etsu, as "Trefil" by Dow Coming or as "Gransil" by General Electric.

Preferably, the composition of the invention can also contain one or more fillers (pulverulent constituents) which can be chosen, for example, from the group formed by talc; micas of natural or synthetic origin; kaolin; zinc oxide or titanium oxide; calcium carbonate; magnesium carbonate and hydrocarbonate; silica, in particular spherical silica, the silica powder sold as "Cab-O-Sil TS 530" by Cabot, and silica microbeads such as those sold as SB150 by Myoshi; titanium dioxide; glass beads and ceramic beads sold by 3M under the trade name "Macrolite"; metal soaps derived from organic carboxylic acids containing from 8 to 22 carbon atoms, preferably from 12 to 18 carbon atoms, for example zinc, magnesium or lithium stearate, zinc laurate, magnesium myristate; non-expanded synthetic polymer powders, such as powders of polyethylene, of polystyrene, of polyesters, of polyamides (for example Nylon or poly-β-alanine), of acrylate copolymers (for example the microporous microspheres sold by Dow Coming under the trade name "Polytrap"), of polymethacrylic acids, of polystyrene or of Teflon, such as "Fluon"; expanded powders such as hollow microspheres made of a thermoplastic material, prepared by known processes, for example those described in U.S. Pat. No. 3,615,972, incorporated herein by reference, and EP-A-056,219, incorporated herein by reference, and in particular the microspheres sold as "Expancel" by Kemanord Plast or as "Micropearl F 80 ED" by Matsumoto; powders of natural organic materials such as crosslinked or non-crosslinked corn, wheat or rice starch, such as the powders of starch crosslinked with octenyl succinic anhydride which are sold as "Dry-Flo" by National Starch; silicone resin microbeads, such as those sold as "Tospearl" by Toshiba Silicone, and mixtures thereof.

The fillers can represent up to 20% by weight relative to the total weight of the composition, and preferably from 1 to 12% by weight relative to the total weight of the composition. These ranges includes all specific values and subranges therebetween, such as 0.1, 0.2, 0.5, 2, 3, 5, 8, 10 and 15% by weight.

The aqueous phase of the composition of the invention represents at least 30% by weight and preferably from 50 to 80% by weight relative to the total weight of the composition. These ranges includes all specific values and subranges therebetween, such as 35, 40, 45, 60, 70, and 75% by weight.

The composition according to the invention can be used in any field in which this type of pharmaceutical form is advantageous, and in particular in cosmetics and dermatology. When it constitutes a cosmetic and/or dermatological composition, it advantageously contains a physiologically acceptable medium, i.e. a medium which is compatible with the skin, mucous membranes, the nails and/or the hair.

The compositions which are the subject of the invention can be applied to a large number of treatments of the skin, mucous membranes (lips) and the hair, including the scalp, in particular for protecting, caring for, cleansing and/or making up the skin and/or mucous membranes, for protecting, caring for and/or cleansing the hair and/or for therapeutically treating the skin, the hair and/or mucous membranes.

The compositions according to the invention can be used, for example, as treatment, care, protection and/or cleansing products for the skin in the form of creams or milks, or as make-up products (for the skin and lips) by incorporation of fillers and/or dyestuffs (pigments and/or dyes). They are particularly suitable for treating wrinkles and/or fine lines of the skin and for treating and/or protecting dry skin.

Thus, the present invention also includes the cosmetic use of the composition as defined above for treating, protecting, caring for and/or cleansing the skin, mucous membranes and/or the hair, and/or for making up the skin and/or mucous membranes.

The present invention also includes the cosmetic use of the composition as defined above for treating wrinkles and/or fine lines of the skin.

The present invention also includes the use of the composition as defined above for the manufacture of a composition intended for treating and/or protecting dry skin.

In addition, as is well-known, the compositions of the invention can contain adjuvants that are common in cosmetics or dermatology, such as hydrophilic or lipophilic active agents, preserving agents, antioxidants, fragrances, solvents, sunscreens, dyestuffs, basic or acidic agents and lipid vesicles. These adjuvants are used in the usual proportions in cosmetics or dermatology, and, for example, from 0.01 to 30% of the total weight of the composition, and, depending on their nature, they are introduced into the aqueous phase or into the oily phase of the composition, or alternatively into vesicles. These adjuvants, and their concentrations, should be such that they do not modify the property which is desired for the composition.

If it is desired to obtain a less fluid composition and/or to improve the stability of the emulsion, one or more hydrophilic gelling agents such as carboxyvinyl polymers or carbomers and polyacrylamides can be added thereto. These gelling agents are used at concentrations generally ranging from 0.05 to 2%, preferably 0.1 to 0.5%, by weight relative to the total weight of the composition.

As active agents which can be used in the composition of the invention, mention may be made, for example, of moisturizers such as polyols and in particular glycerol, ethylene glycol, isoprene glycol, 1,2-propanediol, diglycerol, sorbitol, polyethylene glycols and mixtures thereof.

The composition according to the invention can be advantageously prepared using, for at least one step of the process, a blending machine such as a roll mill comprising two rollers rotating in opposite directions, between which the paste passes, or a mixer-screw extruder. A mixer-screw extruder is preferably used.

Another aspect of the invention is thus a process for preparing a composition according to the invention, characterized in that at least one step of the process is carried out using a mixer-screw extruder.

According to a first embodiment of the invention, the preparation process comprises the following steps:
  (1) preparation of the oily phase in the form of a soft paste obtained by preparing a premix of the waxes and oils, heating this premix to a temperature at which it melts and then introducing the molten premix and the other constituents (in particular the fillers) of the oily phase into a mixer-screw extruder subjected to a temperature gradient ranging from 80° C. to 20° C., in one or more portions, and blending the mixture obtained while at the same time cooling it to room temperature while it is conveyed to the outlet of the mixer-extruder;
  (2) incorporation of the emulsifier and optionally the co-emulsifier into the soft paste obtained in (1), and
  (3) incorporation, with stirring, of the mixture obtained in (2) into the aqueous phase.

In this embodiment, steps (2) and (3) are carried out in a mixing machine usually used by a person skilled in the art, such as a rotor-stator.

In addition, in the process described above, the emulsifier used is an anionic emulsifier which is liquid at room temperature and the amounts used are such that the emulsion obtained comprises at least 5% of wax by weight relative to the total weight of the composition.

As indicated above, since the mixing of the oily and aqueous phases is carried out without heating, the incorporation of heat-sensitive compounds poses no problem.

According to one particular embodiment of the invention, steps (2) and (3) above are also carried out in the mixer-screw extruder used for step (1). The emulsifier and the aqueous phase are then introduced into a section (or element) of the mixer-extruder in which the temperature is close to room temperature.

The use of a mixer-extruder makes it possible to reproducibly obtain a paste of oily phase of very constant quality. Furthermore, it is possible, by adapting the outlet die of the mixer-extruder, to package the composition in-line at the outlet of the said mixer-extruder.

The various steps of the process can be carried out in one or more extruders arranged one after the other, and preferably in a single twin-screw extruder.

The conditions under which the extrusion can be carried out are described in document FR-A-2,715,306, incorporated herein by reference.

Having generally described this invention, a further understanding can be obtained by reference to certain specific examples which are provided herein for purposes of illustration only and are not intended to be limiting unless otherwise specified.

EXAMPLES

Example

Care cream

| Oily phase | | |
|---|---|---|
| Dry-Flo (filler) | | 15% |
| Microcrystalline wax | | 19% |
| Mineral oil | qs | 100% |
| O/W emulsion | | |
| Oily phase | | 20% |
| Hostaphat CG 120 (emulsifier) | | 3% |
| Carbomer | | 0.2% |
| Water | qs | 100% |

Procedure 1:

The mixture of wax and oil is heated to about 100° C., the molten mixture is introduced into a mixer-extruder at the same time as the filler, and the oily phase is obtained at the mixer-extruder outlet in the form of a soft paste, the emulsifier is incorporated into the soft paste in a rotor-stator, next, the mixture obtained is incorporated portionwise into the aqueous phase (water and carbomer) with stirring.

Procedure 2:

The mixture of wax and oil is heated to about 100° C., the filler is introduced into the top element of a mixer-extruder comprising at least six elements, the oily phase is introduced into the second element of the said mixer-screw extruder, and the aqueous phase and the emulsifier are introduced, via two different inlets, into the fourth element of the said mixer-screw extruder.

The elements of the mixer-screw extruder used are, going from the first to the sixth element, maintained at the following respective temperatures: 20° C., 80° C., 60° C., 20° C., 20° C. and 20° C.

A cream which has a very light texture and good moisturizing properties and which is capable of smoothing out the skin's relief is obtained.

Obviously, additional modifications and variations of the present invention are possible in light of the above teachings. It is therefore to be understood that within the scope of the appended claims, the invention may be practiced otherwise than as specifically described herein.

This application is based on French Patent Application Ser. No. 98-15293, filed on Dec. 3, 1998, and incorporated herein by reference in its entirety.

What is claimed is:

1. a method of preparing a creamy composition in the form of an oil-in-water emulsion, said composition comprising:

an oily phase dispersed in an aqueous phase, at least one anionic emulsifier which is a liquid at room temperature, and at least 5% by weight, relative to the total weight of the composition, of at least one wax, wherein the oily phase is in the form of a soft paste at room temperature formed in a mixer-screw extruder, said method comprising:

(a) preparing the oily phase in the form of a soft paste by mixing the waxes and oils, (b) heating the oily phase to a temperature at which it melts, (c) introducing melted oily phase and the other constituents of the oily phase into a mixer-screw extruder subjected to a temperature gradient ranging from 80° C. to 20° C., (d) blending the mixture obtained while it is conveyed to the outlet of the mixer-screw extruder to produce a soft paste, (e) incorporating the emulsifier and, optionally, if present, the co-emulsifier into the soft paste obtained from (d), and (f) incorporating the mixture from (e) into the aqueous phase, to thereby obtain said composition.

2. The method of claim 1, wherein (e) and (f) are conducted in the mixer-screw extruder used in (c)–(d).

3. The method of claim 1, wherein the soft paste has a dynamic viscosity at 25° C. of between 3 and 35 Pa.s as measured with a Contraves TV rotary viscometer fitted with an MS-r4 rotor at a frequency of 60 hz.

4. The method of claim 1, wherein the emulsifier is selected from the group consisting of anionic surfactants containing a phosphate group.

5. The method of claim 1, wherein the emulsifier is selected from the group consisting of mono-, di- and/or triesters of phosphoric acid and of a fatty alcohol having a fatty chain containing from 12 to 22 carbon atoms, and mono-, di- and/or triesters of phosphoric acid and of an ethoxylated fatty alcohol, having a fatty chain containing from 12 to 22 carbon atoms and a number of ethoxylated units ranging from 1 to 100.

6. The method of claim 1, wherein the emulsifier is selected from the group consisting of oleyl phosphate, trioleyl phosphate, dilaureth-4 phosphate, trioleth-8 phosphate, triceteareth-4 phosphate, the monoester of phosphoric acid and of stearic and isostearic acid, and mixtures thereof.

7. The method of claim 1, wherein the amount of emulsifier ranges from 0.1 to 10% by weight of active material relative to the total weight of the composition.

8. The method of claim 1, wherein the composition further comprises a co-emulsifier.

9. The method of claim 8, wherein the co-emulsifier is selected from the group consisting of fatty alcohols containing a branched or unsaturated chain containing from 8 to 22 carbon atoms, fatty acids containing a branched or unsaturated chain containing from 8 to 22 carbon atoms, and mixtures thereof.

10. The method of claim 4, wherein the amount of co-emulsifier ranges from 0.1 to 10% by weight of active material relative to the total weight of the composition.

11. The method of claim 1, wherein the wax is selected from the group consisting of mineral waxes, animal waxes, plant waxes, hydrogenated oils, fatty esters and glycerides which are solid at 25° C., synthetic waxes, silicone waxes, and mixtures thereof.

12. The method of claim 1, comprising at least one wax having a starting melting point of greater than or equal to 50° C.

13. The method of claim 1, wherein the wax is selected from the group consisting of carnauba wax, polyethylene waxes with a starting melting point of greater than 65° C., microcrystalline waxes with a starting melting point of greater than 65° C., and mixtures thereof.

14. The method of claim 1, wherein the amount of wax ranges from 5 to 30% by weight relative to the total weight of the composition.

15. The method of claim 1, wherein the amount of oily phase ranges from 10 to 70% by weight relative to the total weight of the composition.

16. The method of claim 1, wherein the oily phase comprises one or more fatty substances selected from the group consisting of oils of animal origin, oils of plant origin, mineral oils, synthetic oils, fluoro oils, silicone oils, volatile silicone oils, silicone gums, silicone resins, fatty alcohols, fatty acids and silicone elastomers.

17. The method of claim 1, wherein the composition further comprises at least one filler.

18. The method of claim 17, wherein the amount of filler ranges from 1 to 12% by weight relative to the total weight of the composition.

19. The method of claim 1, wherein the aqueous phase represents from 50 to 80% by weight relative to the total weight of the composition.

20. The method of claim 1, further comprising admixing said composition with a physiologically acceptable medium.

21. The method of claim 1, wherein said oils comprise one or more selected from the group consisting of oils of animal origin, oils of plant origin, mineral oils, synthetic oils, fluoro oils, silicone oils and volatile silicone oils.

22. The method of claim 1, wherein said soft paste has a temperature of 20–25° C.

* * * * *

UNITED STATES PATENT AND TRADEMARK OFFICE
CERTIFICATE OF CORRECTION

PATENT NO.    : 6,264,965 B1
DATED         : July 24, 2001
INVENTOR(S)   : Veronique Roulier et al.

It is certified that error appears in the above-identified patent and that said Letters Patent is hereby corrected as shown below:

<u>Column 8, claim 10,</u>
Line 60, "The method of claim 4, wherein the amount of" should read -- The method of Claim 8, wherein the amount of --.

Signed and Sealed this

Fourth Day of December, 2001

Attest:

NICHOLAS P. GODICI
Attesting Officer        Acting Director of the United States Patent and Trademark Office